US008034323B2

(12) United States Patent
Zheng et al.

(10) Patent No.: US 8,034,323 B2
(45) Date of Patent: Oct. 11, 2011

(54) COSMETIC COMPOSITIONS HAVING IN-SITU SILICONE CONDENSATION CROSS-LINKING

(75) Inventors: Tao Zheng, Nanuet, NY (US); Derrick B. McKie, Brooklyn, NY (US); John C. Brahms, Morris Plains, NJ (US); Prithwiraj Maitra, Morristown, NJ (US)

(73) Assignee: Avon Products, Inc., New York, NY (US)

( * ) Notice: Subject to any disclaimer, the term of this patent is extended or adjusted under 35 U.S.C. 154(b) by 1020 days.

(21) Appl. No.: 11/314,633

(22) Filed: Dec. 21, 2005

(65) Prior Publication Data

US 2007/0142599 A1 Jun. 21, 2007

(51) Int. Cl.
*A61Q 1/06* (2006.01)
(52) U.S. Cl. ........................ 424/64; 424/70.12
(58) Field of Classification Search .................. 528/17; 106/287.14; 424/64, 70.12
See application file for complete search history.

(56) References Cited

U.S. PATENT DOCUMENTS

| | | | |
|---|---|---|---|
| 3,757,782 A | 9/1973 | Aiken | |
| 4,196,808 A | 4/1980 | Pardo | |
| 4,202,879 A | 5/1980 | Shelton | |
| 4,578,266 A | 3/1986 | Tietjen et al. | |
| 4,614,675 A * | 9/1986 | Ona et al. | 427/387 |
| 4,699,780 A | 10/1987 | Jennings et al. | |
| 4,781,917 A | 11/1988 | Luebbe et al. | |
| 4,816,261 A | 3/1989 | Luebbe et al. | |
| 4,832,944 A | 5/1989 | Socci et al. | |
| 4,915,938 A * | 4/1990 | Zawadzki | 424/70.122 |
| 4,935,228 A | 6/1990 | Finkenaur et al. | |
| 5,089,253 A * | 2/1992 | Halloran | 424/47 |
| D326,606 S | 6/1992 | Green | |
| 5,225,195 A | 7/1993 | Soyama et al. | |
| 5,318,203 A | 6/1994 | Iaia et al. | |
| 5,318,775 A | 6/1994 | Shore et al. | |
| 5,340,569 A | 8/1994 | Elliott et al. | |
| 5,342,134 A | 8/1994 | Lombardi et al. | |
| 5,424,061 A | 6/1995 | Pappas et al. | |
| 5,475,076 A | 12/1995 | Braun et al. | |
| 5,482,547 A | 1/1996 | Bugnon | |
| 5,533,823 A | 7/1996 | Pierpont et al. | |
| 5,607,665 A | 3/1997 | Calello et al. | |
| 5,688,831 A | 11/1997 | El-Nokaly et al. | |
| 5,747,017 A | 5/1998 | Nichols et al. | |
| 5,863,523 A | 1/1999 | Socci et al. | |
| 5,977,217 A | 11/1999 | Socci et al. | |
| 5,984,554 A | 11/1999 | Bouix | |
| 6,013,682 A * | 1/2000 | Dalle et al. | 516/55 |
| 6,074,654 A | 6/2000 | Drechsler et al. | |
| 6,117,436 A | 9/2000 | Flemming et al. | |
| 6,126,952 A | 10/2000 | Socci et al. | |
| 6,239,211 B1 * | 5/2001 | Keeping et al. | 524/588 |
| 6,247,586 B1 | 6/2001 | Herzog et al. | |
| 6,261,576 B1 | 7/2001 | Fishman | |
| 6,290,935 B1 | 9/2001 | Masters et al. | |
| D449,224 S | 10/2001 | Kaufman | |
| 6,352,699 B1 | 3/2002 | Mondet et al. | |
| 6,383,502 B1 * | 5/2002 | Dunshee et al. | 424/401 |
| 6,428,797 B2 | 8/2002 | Fishman | |
| 6,471,950 B1 | 10/2002 | Farer et al. | |
| 6,471,985 B2 * | 10/2002 | Guyuron et al. | 424/445 |
| 6,509,009 B2 | 1/2003 | Nichols et al. | |
| 6,512,072 B1 * | 1/2003 | Gantner et al. | 528/34 |
| 6,514,483 B2 | 2/2003 | Xu et al. | |
| 6,770,266 B2 | 8/2004 | Santarpia, III et al. | |
| 6,780,402 B1 | 8/2004 | Agostini et al. | |
| 6,789,971 B2 | 9/2004 | Tsaur | |
| 6,824,704 B2 | 11/2004 | Chadwick et al. | |
| 7,198,205 B1 * | 4/2007 | Solomon et al. | 239/337 |
| 7,740,664 B2 * | 6/2010 | Benabdillah | 8/405 |
| 2004/0105874 A1 * | 6/2004 | Bott et al. | 424/401 |
| 2004/0165935 A1 | 8/2004 | Kauffmann et al. | |
| 2005/0000531 A1 | 1/2005 | Shi | |
| 2005/0197477 A1 | 9/2005 | O'Brien et al. | |

FOREIGN PATENT DOCUMENTS

| EP | 90311291.0 | 10/1990 |
|---|---|---|
| GB | 2 407 496 | * 4/2005 |

OTHER PUBLICATIONS

Jens Uhlemann et al., "Flavor Encapsulation Technologies: An Overview Including Recent Developments", Perfumer and Flavorist, Vo. 27, 52-61 (2002).
R. Sparks and I. Jacobs, "Selection of Coating and Microencapsulation Processes", Controlled-Release Delivery Systems for Pesticides, Herbert B. Scher ed., 3-29, (1999).
Cosmestic, Science, and Technology, vol. 1, 27-104 edited by Balsam and Sagarin (1972).
C. Todd and T. Byers, "Volatile Silicone Fluids for Cosmetics", Cosmetics and Toiletries, vol. 91 27-32 (1976).

* cited by examiner

*Primary Examiner* — Margaret Moore
(74) *Attorney, Agent, or Firm* — Joan M. McGillycuddy; Charles S. Zeller

(57) ABSTRACT

Compositions and methods for the in situ formation of cross-linked organosiloxane films are disclosed. The disclosed films are long-lasting, flexible, transfer-resistant, water-resistant and oil-resistant. The film-forming compositions generally comprise alkoxy-terminated organosiloxane polymers and a catalyst and are useful for formulating cosmetics and personal care products.

1 Claim, No Drawings

COSMETIC COMPOSITIONS HAVING IN-SITU SILICONE CONDENSATION CROSS-LINKING

FIELD OF INVENTION

The present invention relates generally to compositions and methods for forming films on a surface. More particularly, the invention relates to films formed by in situ cross-linking of organosiloxane polymers.

BACKGROUND OF THE INVENTION

Many cosmetics and personal care products employ various film forming agents to aid in spreading and adhering a formulation to a surface such as skin. The class of polymers known as organosiloxanes, including polydimethylsiloxane (PDMS or Dimethicone), have recently received considerable attention as film-formers in cosmetic products due to their excellent spreading properties and biological inertness. Examples of cosmetic formulations including organosiloxane film formers include, for example, U.S. Pat. No. 6,780,402 (L'Oreal), U.S. Pat. No. 5,318,775 (Mary Kay Cosmetics), U.S. Pat. No. 4,699,780 (Estee Lauder); and U.S. Pat. No. 4,578,266 (Revlon). In the case of the foregoing patents, the organosiloxane polymers do not undergo cross-linking to form more robust films when applied to a surface and therefore are of limited durability, transfer resistance, and water-resistance.

Recently, in situ cross-linking organosiloxane film formation has been described in U.S. Pat. No. 6,512,072, the contents of which is hereby incorporated by reference. The described film-forming compositions comprise 5 to 79.9 weight % of an alkylene trialkoxy terminated polysiloxane; 0.01 to 5 weight % of a catalyst; 20 to 94.99 to weight % of a volatile diluent, and, optionally, 0.01 to 5 weight % of an alkoxysilane and 0.1 to 25 weight % of a filler.

Despite the advances in film forming methods and compositions, there remains a need in the art for in situ cross-linked organosiloxane film formers which provide long-lasting, comfortable, highly flexible, tack-free, and water-proof films.

It is therefore an object of the invention to provide compositions and methods for forming in situ cross-linked organosiloxane films.

It is further an object of the invention to provide cosmetic and personal care compositions comprising in situ cross-linked organosiloxane films.

SUMMARY OF INVENTION

In accordance with the foregoing objectives and others, the present invention overcomes the deficiencies associated with the prior art by providing elastomeric films for use in cosmetics which are highly flexible yet durable and provide a heretofore unobtainable level of comfort to the user.

In one aspect of the invention, a method for forming an elastomeric film on a biological surface is provided. The biological surface may be any surface to which cosmetics or personal care products are typically applied, including without limitation skin, lips, hair, nails and the like. The method comprises contacting the biological surface with a siloxane polymer and a cross-linking catalyst in the presence of water. The siloxane polymer will have at least one alkoxy-functionalized terminal group or alkoxy-functionalized side chain. Upon application of the siloxane polymer and a cross-linking catalyst to the surface, in the presence of water, the cross-linking catalyst induces in situ cross-linking of the siloxane polymer through polycondensation of the terminal group or side chain. The resultant elastomeric film is water-resistant and long-lasting.

In another aspect of the invention, a method for entrapping a functional agent within an elastomeric film disposed on a biological surface is provided. The method comprising contacting the biological surface with a functional agent, a siloxane polymer, and a cross-linking catalyst in the presence of water. The functional agent may be any agent which is desired to be held in intimate contact with the surface, including without limitation pigments, pharmaceuticals, cosmeceuticals, UV absorbers and the like. The siloxane polymer will have at least one alkoxy-functionalized terminal group or alkoxy-functionalized side chain. Upon application of the siloxane polymer and a cross-linking catalyst to the surface, in the presence of water, the cross-linking catalyst induces in situ cross-linking of the siloxane polymer through polycondensation of the terminal group or side chain. The resultant film is highly elastomeric, water-resistant, and durable and thereby prevents migration or transfer of the functional agent from the biological surface. The film serves to prevent migration or transfer of the active agent by either entrapping the agent within the polymeric network or forming an adhesive film over the active agent which holds it against the surface.

In a further aspect of the invention, formulations for providing an elastomeric film on a biological surface are provided. In one implementation, a one-part formulation is provided comprising an anhydrous composition comprising (i) a siloxane polymer; the siloxane polymer having at least one alkoxy-functionalized terminal group or alkoxy-functionalized side chain; and (ii) a cross-linking catalyst. Upon application to the biological surface, the cross-linking catalyst induces in situ cross-linking of the siloxane polymer in the presence of water, through polycondensation of the terminal group or side chain to provide a highly elastomeric, water-resistant, and long-lasting film thereon. Alternatively, the formulation may be a two-part system comprising (i) a first component comprising a siloxane polymer; the siloxane polymer having at least one alkoxy-functionalized terminal group or alkoxy-functionalized side chain; and (ii) a second component comprising a cross-linking catalyst. The first and second components are prevented from coming into intimate contact prior to use. Upon application to a surface, the cross-linking catalyst induces in situ cross-linking of the siloxane polymer in the presence of water, through polycondensation of the terminal group or side chain to provide a highly elastomeric, water-resistant, and long-lasting film thereon.

These and other aspects of the present invention will become apparent to those skilled in the art after a reading of the following detailed description of the invention, including the illustrative embodiments and examples.

DETAILED DESCRIPTION

The present invention is founded on the discovery that certain cross-linked siloxane polymers are capable of providing flexible cosmetic films on biological surfaces which are long wearing, transfer resistant, waterproof, tack-free, and comfortable to the wearer. The films are formed in situ on the biological surface upon application thereto, meaning that the cross-linking reaction occurs on the surface after application of the film. As used herein, the term "biological surface" is meant to include any surface to which cosmetic and personal care products are applied, including without limitation skin, lips, keratin fibers (eyelashes, eyebrows, or hair), and nails.

a. Film Forming Compositions

An essential component of the invention is a siloxane polymer which is capable of undergoing a condensation reaction in the presence of water and catalyst. In the broadest sense of the invention, the selection of siloxane polymer is not particularly limited. However, the polymer will include at least one side chain or terminal group comprising an alkoxy functional group. In the presence of water, the siloxane polymer undergoes metal catalyzed in situ cross-linking by condensation of the alkoxy terminated moieties. Typically, suitable siloxane polymers are organopolysiloxanes having the structure shown in formula I:

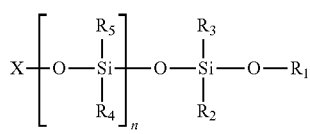

I wherein $R_1$ is a branched or straight chain $C_1$-$C_{10}$ alkyl group, including without limitation methyl, ethyl, propyl, isopropyl, butyl, isobutyl, or t-butyl. With due regard for the kinetics of the polycondensation reaction, $R_1$ is preferably a methyl or ethyl group, and most preferably $R_1$ is methyl group, so as to provide a highly reactive alkoxy terminus for efficient and rapid cross-linking.

$R_2$ and $R_3$ are independently selected from branched or straight chain alkoxy groups, as exemplified by methoxy and ethoxy; substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, n-pentyl, iso-pentyl, neo-pentyl, tert-pentyl, hexyl, vinyl, allyl, butenyl, pentenyl, hexenyl, propynyl, butynyl, pentynyl; cycloalkyl, heterocycloalkyl, haloalkyl, benzyl, alkyl-aryl; substituted or unsubstituted aryl or heteroaryl groups; amino, hydroxyl, hydrido, carboxy, cyano, or halogen. Preferably $R_2$ and $R_3$ are independently selected from methoxy, phenyl, amino, hydroxyl, and carboxy. It will be recognized that, in the case where $R_2$ and/or $R_3$ are alkoxy moieties, the possibility exists for multiple condensation cross-linking reactions to occur. In this manner, so-called "T" and "Q" functionalities can be introduced into the polymer through cross-linking.

$R_4$ and $R_5$ are independently selected from substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, hydroxyl, hydrido, carboxy, cyano, or halogen. Preferably $R_4$ is methyl.

"X" represents any chain terminating group, including without limitation substituted or unsubstituted branched or straight chain $C_1$-$C_{20}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, hydroxyl, carboxy, cyano, hydrido, or halogen; alklysilyl, dialkylsilyl and trialkylsilyl, as exemplified by trimethylsilyl and triethylsilyl.

"n" represents any integer greater than 3 and will typically be between about 3 and about 5,000 and is preferably selected to provide a polymer having a molecular weight of about 800 to about 550,000 g/mol. As will be evident to the skilled artisan, the viscosity of the organosiloxane polymer can be varied by controlling the degree of polymerization and the ratio of T and Q structures. In this regard, suitable organosiloxane polymers will typically have a viscosity of about 5 up to about 20,000,000 centiStokes at 25° C.

The polymer may further comprise monomers having branching points of the T or Q type. When present, the T and Q structures will typically represent less than about 50%, preferably less than about 20%, and more preferably less than about 10% of the total repeat units in the cross-linked organopolysiloxane polymer.

The organosiloxane polymer may be a homopolymer defined by formula I or block, alternating, or statistical copolymer comprising the polymers of formula I.

In one currently preferred embodiment of the invention, the organosiloxane polymer comprises a polydimethylsiloxane polymer (i.e., $R_4$ and $R_5$=methyl). Preferably, the polydimethylsiloxane polymer has one or more methoxy-functionalized terminal groups or side chains (i.e., $R_1$=methyl and/or one or more of $R_2$, $R_3$, $R_4$ and $R_5$=methoxy). In selecting $R_1$, $R_2$ and $R_3$, the skilled artisan will be further guided by the observation that the present invention does not embrace alkylene trialkoxy terminated polysiloxanes.

The organosiloxane polymer condensation reaction is illustrated below in the non-limiting case of a polydimethylsiloxane polymer having a methoxy-functionalized terminus.

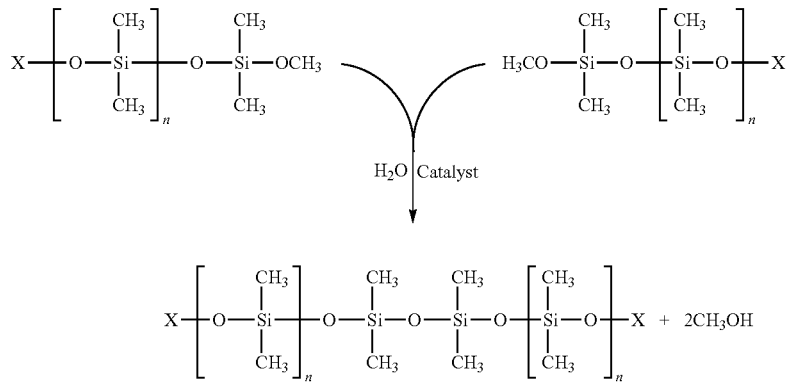

The catalyst may be any catalyst capable of affecting the condensation reaction. Preferably, the catalyst is one which is capable of initiating the condensation reaction at or below body temperature so as to achieve rapid cross-linking (i.e., about 5 seconds to about 5 minutes). Titanium catalysts and zirconium catalysts have been found to be suitable for the practice of the invention.

Suitable titanium catalysts include without limitation alkyl titanates, including, for example, methyl titanate, ethyl titanate, n-propyl titanate, isopropyl titanate, n-butyl titanate, n-butyl titanate polymer, t-butyl titanate, 2-ethylhexyl titanate, and mixed alkyl tinatates; titanate esters, titanium acetylacetonates, acid titatnium chelates including lactic acid titanium chelate, alkoxy titanates, alchohol titanium complexes, and the like.

Suitable zirconium catalysts include the alkyl zircoates and zirconate esters, for example, methyl zirconate, ethyl zircoate, n-propyl zircoate, isopropyl zircoate, n-butyl zircoate, 2-ethylhexyl zircoate, tetra n-butyl zircoate, tetra n-propyl zircoate, mixed alkyl zircoate esters and the like.

A class of industrial products suitable for use are the Tyzor® (DuPont) line of titanium and zirconium catalysts. Most preferred are t-butyl titanate and t-butyl zirconate because they have been found to possess the best balance of moisture resistance and reactivity.

Water is essential to the condensation reaction and therefore the reactive organosiloxane polymer must be kept anhydrous prior art application, or alternatively, must be kept apart from the catalyst prior to application.

b. Film Forming Systems

In accordance with another aspect of the invention, film forming systems comprising the film forming compositions are provided. The film forming systems are designed to prevent the cross-linking reaction from occurring prior to application yet provide convenient means for application. The film forming systems are generally one-part systems or two-part systems.

i. One-Part Systems

In a one-part system, the reactive organosiloxane polymer and catalyst will necessarily be packaged together. Various methods for preventing the cross-linking reaction from occurring prior to application may be envisaged, all of which are contemplated to be within the scope of the invention. However, particular embodiments described below are consider to be currently preferred.

In one embodiment, the reactive organosiloxane polymer and catalyst are packaged together in an anhydrous state. There is essentially no constraint on the amount of catalyst that will be present in the composition. Typically, the catalyst will be present in a ratio to the organosiloxane polymer of about 1:1,000 to about 1:5. It may be desirable to employ an amount of catalyst toward the higher end of this range to account for the fact that diffusion in a viscous film is limited. A preferred range is about 1:100 to about 1:10.

A one-part silicone condensation cross-linking system is commercially available as Dow Corning 7-5300 Film-in-Place Coating. One-part Room Temperature Vulcanising (RTV) Rubbers from GE and Dow Corning are also contemplated to be useful silicone condensation cross-linking system for the one-part systems of the invention. Such single part systems consist of a polydialkylsiloxane with terminal hydroxyl groups, which are reacted with organosilicone cross-linking agents. This operation is carried out in a moisture-free environment and results in the formation of a tetrafunctional structure. Curing takes place when materials are exposed to moisture. Atmospheric moisture is sufficient to trigger the reaction. For example, RTV167™, TSE392-C™, and XE11-B1002™ from GE are one-part room temperature condensation cross-linking systems.

Preferably, an inert carrier is also present to solubilize the reactive organosiloxane polymer and catalyst and provide for efficient application. There is essentially no constraint on the selection of carrier. However, the carrier should be anhydrous, unreactive in the presence of the reactive organosiloxane polymer and catalyst, and compatible with a cosmetic or personal care product. Suitable carriers include, for example, hydrocarbon oils, including without limitation $C_8$-$C_{20}$ hydrocarbons such as isododecane, and silicone oils including without limitation hexamethyldisiloxane (HMDS), polydimethylsiloxane(dimethicone)polymers, and cyclodimethicones. Suitable non-volatile dimethicone polymers are available from Dow Corning under the name Dow Corning 200®. Fluid and have viscosities ranging from 5 to 600,000 centiStokes at 25° C.

Non-polar, volatile oils particularly useful in the present invention are selected from the group consisting of silicone oils; hydrocarbons; and mixtures thereof. Such non-polar, volatile oils are disclosed, for example, in Cosmetics, Science, and Technology, Vol. 1, 27-104 edited by Balsam and Sagarin, 1972. The non-polar, volatile oils useful in the present invention may be either saturated or unsaturated, have an aliphatic character and be straight or branched chained or contain alicyclic or aromatic rings. Examples of preferred non-polar, volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals.

Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of cyclomethicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.).

Suitable non-volatile, non-polar emollients for use in the compositions of the invention are disclosed, for example, in Cosmetics, Science, and Technology, Vol. 1, 27-104 edited by Balsam and Sagarin, 1972; U.S. Pat. No. 4,202,879; and U.S. Pat. No. 4,816,261, the disclosures of which are hereby incorporated by reference. Non-volatile oils useful in the present invention are essentially non-volatile polysiloxanes, paraffinic hydrocarbon oils, and mixtures thereof. Suitable polysiloxanes useful in the present invention are selected from the group consisting of polyalkylsiloxanes, polyarylsiloxanes, polyalkylarylsiloxanes, poly-ethersiloxane copolymers, and mixtures thereof. Special mention may be made of polydimethyl siloxanes having viscosities of from about 1 to about 600,000 centistokes at 25° C., including without limitation the Viscasil series of polyalkylsiloxanes (General Electric Company) and the Dow Corning 200 series (Dow Corning Corp.). Suitable polyalkylarylsiloxanes include polymethylphenyl siloxanes having viscosities of from about 15 to about 65 centistokes at 25° C. such as, for example, those available as SF 1075 methyl-phenyl fluid (General Electric Company) and 556 Cosmetic Grade Fluid (Dow Corning Corp.). Useful polyethersiloxane copolymers include, without limitation, a polyoxyalkylene ether copolymer having a viscosity of about 1200 to 1500 centistokes at 25° C., including for example SF1066 organosilicone surfactant (General Electric Company).

The carrier will typically comprise from about 10% to about 90% by weight of the film-forming composition, and more typically between about 30% and about 80% by weight. In preferred embodiments, the carrier comprises between about 50% and about 70% by weight of the film-forming composition.

The one-part anhydrous systems may be packaged in any conventional manner, including bottles, tubes, tubs, and the like. However, such products may be limited to one-time use because ambient moisture introduced into the packaging through opening and closing will initiate the cross-linking reaction in the unused portion. When so packaged the composition may be applied to the biological surfaces with any type of applicator known in the art, including sprays, swabs, brushes, towelets, and applicator tips integral with the package. The compositions will rapidly react on the surface due to the presence of moisture in the air or on the surface to form a cross-linked film with excellent adherent properties.

In such one-part systems requiring anhydrous conditions, multi-use systems may also be prepared by incorporating the film-forming compositions in sealed dispensers which prevent ambient moisture from entering the packaging during application. In this regard, particular mention may be made of the cosmetic dispensers disclosed in U.S. Pat. Nos. 5,533,823, 5,984,554, and 5,342,134, the disclosure of which are hereby incorporated by reference. Spray packaging, as aerosols or pumps, may also be ideally suited for this application.

While the foregoing anhydrous one-part systems are within the scope of the invention, it is preferred to provide one-part systems which do not depend on the maintenance of an anhydrous condition. Such systems will provide multi-use products which do not require special packaging to avoid the introduction of moisture. In one interesting implementation of the invention, the film-forming system is a one-part, multi-use system comprising a continuous phase of reactive organosiloxane polymer dissolved in a carrier medium and a disperse phase comprising a plurality of microcapsules having the catalyst encapsulated therein. Because the catalyst and organosiloxane polymer are prevented from coming into intimate contact by virtue of the encapsulant, the cross-linking reaction is prevented. Only when the microcapsules are ruptured or otherwise degraded does the catalyst contact the polymer.

As is well known in the art, encapsulating materials can be selected which will release the catalyst upon exposure to moisture, pH change, temperature change, solubility change, or mechanical shear. Suitable encapsulating materials and methods of preparing encapsulated materials, such as spray drying, extrusion, coacervation, fluidized bed coating, liposome entrapment and others, are disclosed in, for example, U.S. Pub. No. 2005/0000531 A1, Jens Uhlmann, Brigit Schleifenbaum, Heinz-Jurgen Bertram, "Flavor encapsulation technologies: an overview including recent developments" *Perfumer and Flavorist,* 27, 52-61, 2002, and "Selection of Coating and Microencapsulation Processes" by Robert E. Sparks and Irwin Jacobs in *Controlled-Release Delivery Systems for Pesticides,* Herbert B. Scher ed., Marcel Dekker, New York, N.Y., 1999, pp 3-29, the contents of which are hereby incorporated by reference. Moisture sensitive microcapsules will suffer the disadvantage of requiring anhydrous conditions prior to use and are therefore less preferred than microcapsules which release their contents by other mechanisms.

ii. Two-Part Systems

In another embodiment of the invention, the reactive organosiloxane polymer and the catalyst are physically separated prior to use. The system may be in the form of a first component comprising the reactive organosiloxane polymer and a second component comprising the catalyst. In this embodiment, it is not necessary to maintain anhydrous conditions in either component. Both the first and second components may further comprise a carrier material, as described above.

The first and second components may be packaged separately, for example in two containers, bottles, tubes, and the like, or may be packaged in one container having a physical partition which prevents the first and second components from coming into contact as described in, for example, U.S. Pub. No. 2004/0165935 A1 and U.S. Design Pat. Nos. D449,224, D326,606 and U.S. Pat. Nos. 6,789,971, 6,247,586, 5,318,203, 4,196,808 and 3,757,782 the contents of which are hereby incorporated by reference.

In use, it is preferred to first apply the component comprising the reactive organosiloxane to a surface as a base coat. Thereafter, the component comprising the catalyst is applied as a top coat over the base coat. The base and top coats are applied onto the surface sequentially with a mixing ratio from about 1:1 to about 5:1. Alternatively, the first and second components may be mixed immediately prior to use and applied as one coating to the surface.

A suitable two-part silicone condensation cross-linking system is commercially available as Dow Corning 7-5310 Base and Dow Corning 7-5311 Curing Agent, which is an in-situ cure elastomer film used in health care industry for scar or wound healing.

c. Products

The film-forming systems may be useful in a variety of cosmetic and personal care products, including without limitation, lipsticks and lipcolors, water-proof mascaras, transfer-resistant foundations, solvent-free nail enamels, water-proof sunscreens and insect repellents, skin care products, hair care products, tooth-whitening products, antiperspirants and deodorants, and other cosmetic products.

Various fillers may be added to reinforce to film forming systems. When present, fillers may be added to the continuous phase of the one-part systems and both the first and second components of the two-part systems. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride;

organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Other useful powders are disclosed in U.S. Pat. No. 5,688,831, the disclosure of which is hereby incorporated by reference.

Where the product is a color cosmetic, such as a lipstick, lip gloss, nail enamel, mascara, foundation, and the like, the compositions will further comprise one or more coloring agents. It is within the skill in the art to choose coloring agents and combinations of coloring agents to produce a desired color. Suitable coloring agents, including pigments, lakes, and dyes, are well known in the art and are disclosed in the C.T.F.A. Cosmetic Ingredient Handbook, First Edition, 1988, the contents or which are hereby incorporated by reference. Organic pigments include, for example, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable colorants include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. The colorants may be surface modified with, for example, fluoropolymers, to adjust one or more characteristics of the colorant as described in, for example, U.S. Pat. Nos. 6,471,950, 5,482,547, and 4,832,944, the contents of which are hereby incorporated by reference. Suitable pearling pigments include without limitation bismuth oxychloride, guanine and titanium composite materials containing, as a titanium component, titanium dioxide, titanium lower oxides or titanium oxynitride, as disclosed in U.S. Pat. No. 5,340,569, the contents of which are hereby incorporated by reference.

In one embodiment, a long-lasting, water-proof, tack-free nail enamel is provided comprising the film-forming systems of the invention. Advantageously, all of the nitro-cellulose commonly found in nail enamels as a film-former can be replaced by the films disclosed herein. Thus, "nitro-cellulose free" nail enamels may be formulated by including the film-forming systems of the invention in place of nitro-cellulose, or other film-forming polymers, in nail formulations such as those described in U.S. Pat. Nos. 6,126,952, 5,977,217, 5,863,523, 5,607,665, 5,424,061, and 5,225,195 the disclosures of which are hereby incorporated by reference.

In another interesting embodiment, the film forming systems of the invention are formulated in lipstick and lipcolor products. Lipsticks and lipcolors may be prepared by including the film-forming systems of the invention in any formulation for such products in place of conventional film-formers. Such conventional lip products include, without limitation, U.S. Pat. Nos. 6,509,009, 6,428,797, 6,261,576, 5,747,017, 5,318,775, and 4,935,228, the disclosures of which are hereby incorporated by reference. The film-forming systems of the present invention are ideally suited for lip products because they are highly resistant to transferring color to objects which come into contact with the lips, such as glasses, cups, including Styrofoam, napkins, clothing, fingers, and the like. Further, the films of the invention are highly flexible which contributes to their long-wearing properties, decreased cracking, and increased comfort as compared to prior art lip products.

In addition to color cosmetics, the films may be incorporated into any product where it is desirable to hold a functional agent in contact with a biological surface. In addition to pigments, lakes, dyes, opacifiers, and pearling agents, the functional agent may be, for example, insect repellants, UV absorbers, UV blockers, antiperspirants, moisturizers, conditioners, tooth whiteners, and the like.

In a further embodiment, the film forming system is formulated into a tooth whitening product. The product may comprise various whitening agents, including for example, chlorine dioxide, hydrogen peroxide, calcium peroxide, metal chlorites, perborates, persulfates, peroxyacids, urea peroxide and percarbonate salts, including sodium percarbonate. Other components suitable for use in tooth whitening products include, but are not limited to those described in U.S. Pat. Nos. 6,824,704, 6,770,266, 6,514,483 and 6,290,935, the disclosures of which are hereby incorporated by reference. The films of the present invention serve to improve the benefits of such tooth whitening compositions by holding the whitening agents against the teeth in a long-lasting and water-resistant film.

The compositions of the invention may optionally comprise other active and inactive ingredients typically associated with any of the foregoing cosmetic and personal care products, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and mixtures thereof. In addition to the foregoing, the personal care products of the invention may contain any other compound for the treatment of skin disorders.

Example 1

A lipgloss according to the invention is provided as a two-part formulation comprising a base coat and a top coat. The base coat comprises the cross-linkable organosiloxane polymer and other ingredients as shown in Table 1.

TABLE 1

| Lip Gloss Base Coat | |
|---|---|
| Dow Corning 7-5310 Base | 70 |
| Cyclopentasiloxane | 20 |
| Pigment Blend | 10 |

The Dow Corning 7-5310 Base comprises a polydimethylsiloxane polymer having reactive trimethoxysilyl end groups, —Si(OCH$_3$)$_3$.

The top coat, which comprises the curing agent, is kept separate from the base coat until application to the lips. Two top coat formulations (Sample 1 and Sample 2) are provided in Table 2.

TABLE 2

| Lip Gloss Top Coat | | |
|---|---|---|
| | Sample 1 | Sample 2 |
| Dow Corning 7-5311 Curing Agent | 70 | 70 |
| Dow Corning 200 ® Fluid (1,000 CST) | 30 | — |
| Dow Corning 200 ® Fluid (30,000 CST) | — | 20 |
| Dow Corning 200 ® Fluid (100,000 CST) | — | 10 |

The top coat comprises the curing agent Dow Corning 7-5311 which contains a t-butyl titanate catalyst. The Dow Corning 200® Fluids employed in the top coats are linear polydimethylsiloxane (dimethicone) polymers of various degrees of polymerization. The dimethicone fluids comprise terminal trimethylsilyl, —Si(CH$_3$)$_3$, groups and are therefore unreactive in the presence of the curing agent. The three dimethicone fluids in Table 2 differ in viscosity (centistokes, "CST"), as shown in Table 2. Thus, the Sample 2 top coat will have a relatively high viscosity as compared to the Sample 1 top coat.

Example 2

The transfer resistance of the lipgloss formulations of Example 1 was examined in comparison to the commercial lip coloring products Lipfinity™ (Procter & Gamble) and Lip Polish™ (Maybelline) using a modification of the transfer resistance testing protocol of U.S. Pat. No. 6,074,654, the disclosure of which is hereby incorporated by reference. The testing protocol is described below.

Transfer Resistance Test Method

This method may be utilized to determine the water and oil transfer resistance and adhesion properties of a cosmetic film. This test predicts the ability of a cosmetic film to resist color transfer to objects contacting the skin. Such objects include clothing, handkerchiefs or tissues, napkins and implements such as cups, glasses and table wear, and oily fingers or objects such as oily foods.

Films formed from cosmetic compositions exhibit a degree of transfer resistance directly proportional to the hardness and solvent-resistance of the film. The hardness and solvent-resistance can be expressed as a function of the blot and rub test as described below. Standard safety measure should be observed when performing this test.

Equipment:
(1) Glass plates;
(2) Collagen sausage casing such as Nippi Casing F Grade;
(3) Constant humidity chamber adjusted to 95% relative humidity;
(4) Utility Knife;
(5) Ruler;
(6) Single-sided adhesive tape;
(7) Double-sided adhesive tape;
(8) 25 micron thickness slot draw-down bar;
(9) White Styrofoam dinner plate such as Amoco Selectables™ Plastic DL® Tableware;
(10) 1.5 inch diameter circular metal punch;
(11) 1 kilogram weight;
(12) Vegetable oil;
(13) Brush-tip cosmetic applicator; and
(14) Lint-Free Wiper, such as Kimwipes® EX-L.

Procedure:
(1) Prepare a 3×4 inch sheet of collagen sausage casing by hydrating it in a 90% relative humidity chamber for at least 24 hours.
(2) Remove the collagen sheet to ambient conditions and immediately wrap tightly around the glass plate. Attach the collagen sheet to the glass using adhesive tape. The collagen surface should be flat and free of wrinkles.
(3) Allow the collagen-wrapped slide to equilibrate at ambient conditions for 24 hours.
(4) Draw down thin (1 mil), uniform films of cosmetic on the collagen surface. The base coat is applied first and the top coat is applied immediately thereafter.
(5) Allow the cosmetic samples on the collagen surface to sit at ambient conditions for one hour.
(6) Using a pipet, drop three drops of vegetable oil onto the right side of the film. Using another pipet, drop three drops of water onto the left side of the film.
(7) Separately for the oil and water sections, distribute the oil and water evenly over the film surface with cosmetic brush applicators, brushing lightly.
(8) Allow the oil and water to remain on the film undisturbed for 15 minutes.
(9) Using a lint-free wiper, carefully blot excess oil and water from the film surface. Apply as little pressure as possible during this step.
(10) Cut two disks from a clean, white Styrofoam dinner plate using a 1.5 inch diameter circular punch. The surface and edges of each disk should be smooth and even.
(11) Firmly attach with double-sided adhesive tape the disks from step (10) to the bottom surface of the 1 kg weight.
(12) Set the weight on top of the cosmetic sample applied to the collagen surface from step (5) above so that disk #1 is in contact with the oil section of the film. And disk #2 is in contact with the water section of the film. It is important to position the weight gently so that excess force beyond 1 kg is not applied.
(13) Grasping the top of the 1 kg weight, carefully rotate the disk through 360 degrees while maintaining the 1 kg force on the film. Do not lift or press the weight into the film during the rotating motion to the weight. The entire 360 degree rotation should be completed within a time interval between 3 and 5 seconds.
(14) Lift the weight straight up off the film surface and carefully remove the disk from the weight avoiding damage to the disk.
(15) Color transfer on individual discs is based on visual assessment of the discs compared to commercial products as positive and negative benchmarks. The positive control used is Lipfinity™ (base coat) while negative control used is the Lip Polish™ product.
(16) The criteria used in the "Star Grading System" for measuring the degree of transfer is explained in Table 3.

TABLE 3

Star Grading System

| Visual Assessment of Transfer | Scale |
|---|---|
| Less than Negative Control | * |
| Equal to or slight better than Negative control | ** |
| Between Negative and Positive Control | *** |
| About equal to positive control | **** |
| Better than positive control | ***** |

The results indicate that the lip gloss formulations of Example 1 exhibit superior transfer resistance to both the positive (Lipfinity™ base coat) and negative (Lip Polish™) controls. In each case noticeably less pigment had transferred to the Styrofoam disk for both formulations of Example 1 than for the control products. The results are quantified on the basis of the Star Grading System as shown below in Table 4.

TABLE 4

| Lip Gloss formulation of Example 1 | Transfer Resistance (Oil) | Transfer Resistance (Water) |
|---|---|---|
| Base Coat (Table 1) plus Top Coat (Table 2, Sample 1) | ***** | ***** |
| Base Coat (Table 1) plus Top Coat (Table 2, Sample 2) | ***** | ***** |

Example 3

The flexibility of the lip gloss formulations of Example 1 were examined using a modification of the flexibility testing protocol described in U.S. Pat. No. 6,074,654, the contents of which are hereby incorporated by reference. The flexibility of a cosmetic film is an important to both the durability (long-wear) and comfort properties of a cosmetic film.

Flexibility is measured by the latex stretch test. This test predicts the ability of the color film to resist flaking or peeling types of failure after application by movement of the skin during normal activities. The flexibility latex stretch test is based on the weight-loss measurement before and after the latex stretch.

Equipment:
(1) Ansell Industrial technicians unlined gloves (12" length, 17 mil) USDA Accepted #390, Size 9;
(2) Slanted Eyeshadow Brushes from Avon Products, Inc.
(3) Analytical balance (4 decimal places); and (4) Ruler.

Procedure:
(1) Cut a 1 inch wide band from the wrist area of the glove, avoiding the ribbing and thumb.
(2) Mark off a 1×1 inch block in the center of smooth side of the band, avoiding the embossed number.
(3) Weigh and record the weight of the latex band; hereinafter referred to as A.
(4) Determine the initial weight of the cosmetic to be applied to the band in order to produce a dried film weighing 20 mg. This is determined by dividing 20 mg by the weight percent of non-volatile material present in the cosmetic. For example, 40 mg of a cosmetic with 50% non-volatile content must be applied to the band in order to yield a 20 mg dried film.
(5) Using a clean eyeshadow brush, evenly apply the amount of cosmetic determined in step (4) over the 1×1 inch area of the band as marked in step (2).
(6) Immediately weigh and record the combined weight of the latex band and applied cosmetic. The weight of wet film with the latex band is referred to as B.
(7) Allow the sample on the latex band from step (6) to sit at ambient room conditions for 24 hours. The optimum test conditions to reliably correlate this test to the physical characteristics of the composition require that the film be dry. By dry it is meant that at least 90% of the volatile carrier of the cosmetic composition has evaporated.
(8) Weigh and record the combined weight of the latex band A and the applied cosmetic film; hereinafter referred to as C. Subtract A from C to determine the dried film weight D (D=C−A). This weight should be 20±2 mg.
(9) Gently stretch the latex band so that the marked film length changes from 1.00 inches to 1.75 inches.
(10) Upon observing loosened film pieces on the latex band, remove the film pieces from the latex band by vigorously wiping a clean eyeshadow brush across the surface of the film: 10 times wiping in vertical direction and 10 times wiping in horizontal direction.
(11) Carefully allow the latex band to return to its approximate original shape.
(12) Record the weight of the latex band (with the remaining cosmetic); herein referred to as E.
(13) A "Star Grading System" is used based on percentage weight loss ("PWL") to grade the flexibility of the films as follows:

TABLE 5

| Weight Loss | Scale |
|---|---|
| 100-50% | * |
| 30-50% | ** |
| 15-30% | *** |
| 5-15% | **** |
| 0-5% | ***** |

The percent weight loss of the cosmetic film is calculated using the following equation:

$$\text{Percent Weight Loss(PWL)} = [1-(E-A)/(C-A)] \times 100\%$$

For some very flexible films, the percentage weight loss may be negligible. Therefore, in some case, due to some dust transferred from the brush, the PWL value may become negative (weight gain).

Steps (1) through (12) are repeated three times for each cosmetic formulation tested. The average of the three PWL values is determined; herein referred to as Average Percent Weight Loss ("APWL"). Low APWL values (i.e., 0-5%) correspond to flexible films having a desirable adhesive and cohesive balance of the film. The flexibility test results for the lip gloss formulations of Example 1 are quantified on the Star Grading System as shown in Table 6.

TABLE 6

| Lip Gloss formulation of Example 1 | Flexibility |
|---|---|
| Base Coat (Table 1) plus Top Coat (Table 2, Sample 1) | ***** |
| Base Coat (Table 1) plus Top Coat (Table 2, Sample 2) | ***** |

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A method for applying a long-wearing, transfer-resistant glossy film to the lips, comprising applying to the lips a base coat comprising a polydimethylsiloxane polymer having reactive trialkoxysilyl endgroups, a volatile silicone, and a coloring agent selected from the group consisting of pigments, lakes and dyes; and applying a top coat over said base coat, the top coat comprising a polycondensation cross-linking catalyst, and a dimethicone fluid that is unreactive in the presence of said catalyst.

* * * * *